Figure 1:
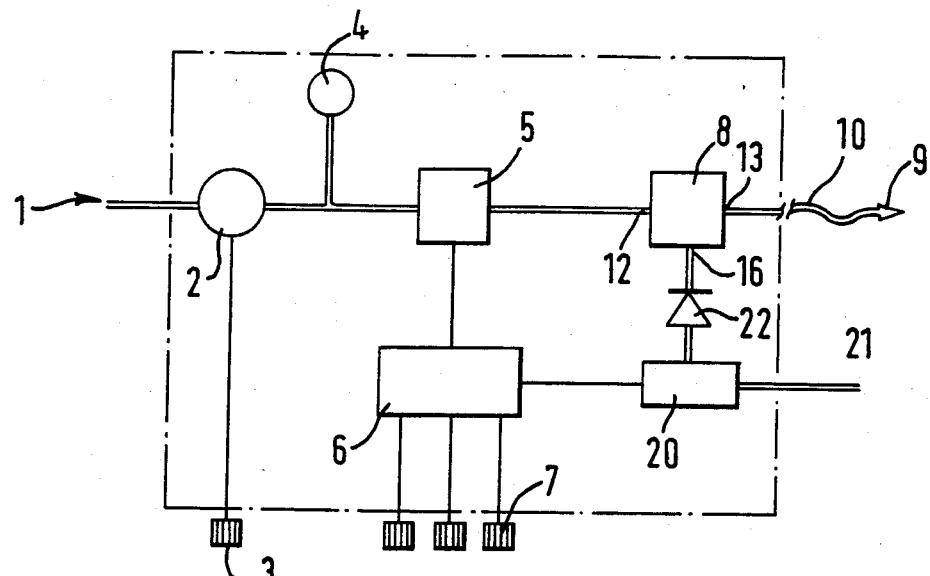

United States Patent [19]

Smith

[11] Patent Number: 4,541,966

[45] Date of Patent: Sep. 17, 1985

[54] GAS HUMIDIFYING APPARATUS AND METHOD

[75] Inventor: Brendan E. Smith, Studley, England

[73] Assignee: Penlon Limited, England

[21] Appl. No.: 643,697

[22] Filed: Aug. 24, 1984

[30] Foreign Application Priority Data

Aug. 25, 1983 [GB] United Kingdom ............... 8322855

[51] Int. Cl.⁴ .......................................... A61M 11/02
[52] U.S. Cl. .................................. 261/27; 128/200.18; 128/200.21; 128/204.25; 261/DIG. 65; 261/76; 261/64 R
[58] Field of Search ...................... 128/204.25, 200.18, 128/200.21; 261/27, DIG. 65, 64 R, 76

[56] References Cited

U.S. PATENT DOCUMENTS

| | | | | |
|---|---|---|---|---|
| 3,221,733 | 12/1965 | Beasley | ........................... | 128/204.25 |
| 3,630,196 | 12/1971 | Bird et al. | ....................... | 128/204.25 |
| 3,812,854 | 5/1974 | Michaels et al. | ............... | 128/200.16 |
| 3,903,884 | 9/1975 | Huston et al. | .................. | 128/200.18 |
| 4,007,238 | 2/1977 | Glenn | ........................... | 261/DIG. 65 |
| 4,484,576 | 11/1984 | Albarda | ........................ | 261/DIG. 65 |

*Primary Examiner*—Tim Miles
*Attorney, Agent, or Firm*—Bacon & Thomas

[57] ABSTRACT

An apparatus and method for humidifying gases, suitable for use in conjunction with a high frequency positive pressure ventilation (HFPPV) respiratory system, includes a nebulizing chamber 11 arranged to receive a pulsed gas flow from an oscillating valve 5 and a liquid reservoir 15 communicating with the chamber 11 such that in use liquid from the reservoir 15 passes into the chamber and is entrained in droplet form by the gas flow. A pump 20 is intermittently operable to introduce a predetermined quantity of liquid into the reservoir 15, and control means 6 of the apparatus are adapted to maintain the valve 5 in its closed condition during operation of the pump 20.

9 Claims, 2 Drawing Figures

GAS HUMIDIFYING APPARATUS AND METHOD

This invention relates to an apparatus and method for humidifying gases, and relates in particular to the humidification of fluctuating gas flows which are supplied to the lungs of a patient in an artificial ventilation system.

In certain instances, for example where a patient has stoppped breathing spontaneously following a severe shock to his system, recent medical research has shown that it is desirable to promote artificial breathing by means of a ventilator which supplies pulses of gas to the lungs which have a considerably higher frequency than the natural frequency of spontaneous respiration. In such a system the pulsed ventilating gas supply is typically supplied directly to the lungs via a narrow orifice jet connected to the end of a length of flexible low compliance tubing adapted to be introduced into the patient's throat. This patient ventilating technique is commonly termed HFPPV (High Frequency Positive Pressure Ventilation) and will be so referred to hereinafter.

Experience has shown that it is essential for successful treatment with HFPPV that the flow of gas into the lungs starts and stops rapidly such that the fluctuating flow aproximates to a square wave. Thus, suitable gas supply apparatus must generally have a relatively low compliance and, moreover, relatively high gas pressures are used. A typical gas supply apparatus for HFPPV therefore supplies to the outlet jet gas pulses having frequencies in the order of 0.5 to 5 Hz and pressures ranging from 100–200 kPa, the precise values being selectable by the physician in accordance with his clinical judgement.

However, problems have been encountered in HFPPV in precisely regulating the temperature, total volume and most significantly the humidity of the gas delivered to the patient. In common with other patient ventilating systems, it is essential that the gas supplied to the lungs in HPPV is humidified to a required degree such that on the one hand substantial and potentially harmful water loss from the lung surfaces is avoided (as may occur if the gas were supplied directly from a compressed gas cylinder or a liquified gas container where the gases are dried to a high degree before storage), while on the other hand the liquid content of the gas does not exceed a certain danger level which can cause the accumulation of excess liquid in the lungs.

There have been several proposals to humidify the gas supplied to a patient in HFPPV, although none of these enables regulated and consistent liquid entrainment over a range of operating parameters. In one method, a suitable entrainment device adjacent the outlet jet is adapted to introduce saturated gas from a separate reservoir into the pulsed gas flow. However, with such a method the total volume flow into the lungs is increased by the entrained gas, and moreover the degree of entrainment depends on lung compliance which may change considerably; as a result precise control of the various gas flow parameters cannot be achieved. In another arrangement water is supplied to the outlet jet in liquid form via a cannula such that water is nebulized by the gas stream and carried into the lungs in droplet form. However in this arrangement problems arise due to cooling at the jet which undesirably increases the size of the droplets; larger droplets do not penetrate the finer lung passages but are deposited in the bronchi and large passages which is ineffective and can be harmful. Clearly, the provision of heat to counteract this effect is difficult at the jet owing to its close proximity to the patient's body tissues.

Accordingly, it has been proposed to provide a humidifying or nebulizing apparatus upstream of the patient supply tube at a position remote from the patient where the apparatus can more conveniently be maintained at a suitable temperature. However, conventional nebulizers or humidifiers often result in liquid being delivered to the patient in bolus form, and moreover the total amount of liquid supplied to the patient cannot be accurately regulated, the difficulty being to control the liquid flow into a humidifying apparatus which has a rapidly and sharply varying internal pressure. Furthermore, known humidifiers generally require a relatively large liquid reservoir in communication with the gas flow, and this results in an increase in the overall system compliance which is undesirable where the required gas flow pattern is a square wave.

Viewed from a first aspect the invention provides gas humidifying apparatus comprising a chamber arranged to receive a fluctuating gas flow from an oscillating valve means, a liquid reservoir communicating with the chamber such that in use liquid from the reservoir passes into the chamber and is entrained in droplet form by the flow of gas, liquid supply means intermittently operable to introduce a predetermined quantity of liquid into the reservoir, and control means adapted to maintain said valve means in a closed condition during operation of said liquid supply means.

Viewed from a second aspect the invention provides a method of humidifying a fluctuating gas flow from an oscillating valve means wherein liquid from a reservoir is entrained in droplet form by the flow of gas in a chamber communicating with said reservoir, comprising intermittently introducing a predetermined quantity of liquid into the reservoir while maintaining said valve means in a closed condition.

Thus in accordance with the invention the oscillating gas supply valve remains closed during refilling of the liquid reservoir, and the gas pressure within the chamber is therefore low and does not fluctuate. In the context of HFPPV apparatus this represents a significant advantage in that the possibility associated with known arrangements of a bolus of liquid being supplied to the patient owing to pressure fluctuations in the apparatus during refilling is removed. The applicability of the humidifying apparatus and method in accordance with the invention to HFPPV systems is based partly on the recognition that a patient is not harmed through intermittent interruption of the gas supply during refilling of the reservoir, and in accordance with the invention several further significant advantages may be achieved. Since the reservoir is continually refilled at intermittent intervals, a relatively small low-compliance reservoir may be used which is important when it is desired to maintain substantially square-wave gas pulses. Moreover, since a known quantity of liquid is introduced into the reservoir during each refilling cycle, a physician can monitor and if necessary regulate the overall quantity of liquid being delivered to the patient over a relatively short period of time, for example several minutes. With systems including large reservoirs, monitoring is only possible over longer periods and serious irregularaties of delivery can occur over short periods of time.

Experience has shown that liquid need not be supplied to the patient continuously during HFPPV, and therefore in accordance with the invention it is acceptable for there to be a time period after the reservoir has emptied before it is refilled; a physician may therefore monitor the overall quantity of liquid being delivered to the patient by regulating firstly the length of time the reservoir remains empty before refilling takes place and secondly the volume of liquid introduced into the reservoir during refilling.

In a preferred embodiment, the liquid is introduced into the reservoir by means of a metered pump, e.g. a piston and cylinder, or a diaphragm or peristaltic pump which is actuable to supply liquid at a predetermined flow rate. The pump preferably communicates with the reservoir via a non-return valve to prevent the reverse flow of liquid when the humidifier is operative and is under positive internal pressure.

It is envisaged that the reservoir may be refilled automatically at appropriate pre-set intervals, depending on the flow rate of the gas supplied to the patient and other relevant parameters; alternatively the physician may apply an element of clinical judgement and may actuate the pump at intermittent intervals depending on the various operating parameters. In either case, the running time of the pump and thus the volume of liquid supplied to the reservoir during each refilling cycle is preferably accurately regulated by suitable control circuitry.

The control means whereby the gas supply valve means is maintained in a closed condition during refilling of the reservoir preferably forms part of control circuitry for the apparatus as a whole which is additionally adapted to control the frequency of the oscillating valve, the operating period of the liquid supply pump, and may also be responsive to various operating parameters such as the temperature of the apparatus and gas pressure. Suitable displays and/or warning indicators may be provided to assist the physician in monitoring the various operating parameters. Means are preferably provided to heat the apparatus and maintain it at a desired preset temperature, such that the droplet size is minimised and the gas supplied to the patient is appropriately warmed.

Any convenient means may be provided in the chamber whereby the liquid from the reservoir is converted into droplets and is entrained in the gas. In a preferred embodiment, the apparatus includes a so-called Bernoulli nebulizer, and liquid is forced from the reservoir into the chamber as a result of increases in gas pressure therein and is introduced into the gas flow within the chamber via a small diameter tube; the liquid is entrained and nebulized by the gas flow, and the droplets then impinge on an anvil which causes a further reduction in their size before they emerge, carried by the gas, via a suitable outlet opening.

In a preferred embodiment, the total volume of the nebulizing chamber and the reservoir is less than 10 ml.

The invention extends to the provision of an HFPPV system incorporating humidifying apparatus as set out above. Such a system may if desired additionally be adapted to deliver drugs to a patient, for example a local anaesthetic for the throat, in which case metered quantities of the desired drugs are added to the liquid either before or after the introduction thereof into the reservoir.

Figure 2:
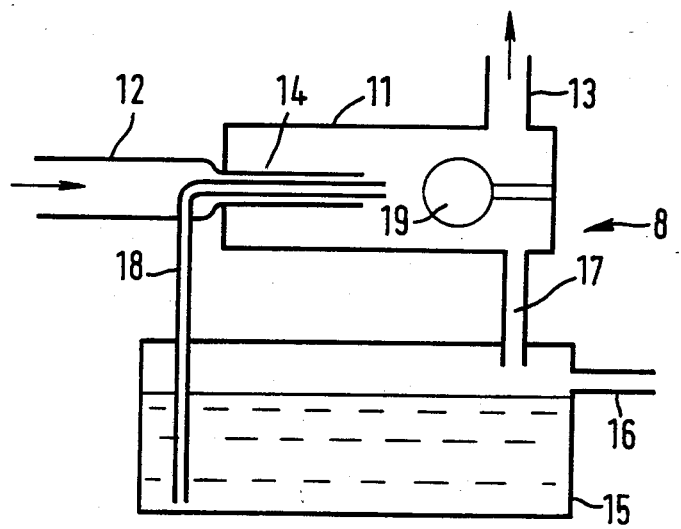

A preferred embodiment of the invention will now be described, by way of example only, with reference to the accompanying drawing wherein:

FIG. 1 is a schematic view of a high frequency positive pressure ventilation system; and FIG. 2 is a schematic view on an enlarged scale of a humidifier.

Referring firstly to FIG. 1, HFPPV apparatus comprises an inlet 1 which is connected in use to a compressed medical gas supply, for example oxygen, air or a mixture of these and/or other gases. The pressure of the gas at the inlet might typically be between 300–450 kPa. Downstream from the inlet 1 is a pressure regulating valve 2 whereby the gas pressure may be reduced by means of a control 3 to the required pressure for supply to a patient, typicaly 100–200 kPa; the reduced system pressure is displayed on a pressure gauge 4.

Downstream from the regulating valve 2 is a solenoid controlled valve 5 which is actuable so as to oscillate between open and shut conditions at a desired frequency by means of control circuitry 6. Two such valves 5 may if desired be provided in series for safety reasons, and may be three-way valves such that in the closed condition, i.e. when the pressurised gas supply is shut off, the downstream part of the system and the line to the patient are open to the atmosphere. Controls 7 are provided such that the frequency of oscillation, the ratio between the open and closed time of the valve, and various other operating parameters may be adjusted. Typically the frequency range of the valve is 0.5 to 5.0 Hz, and the open/shut ratio lies within a range 10:1 to 1:10.

The valve 5 produces gas pulses which approximate to square wave pulses, the volume of gas per pulse being dependent on the selected open time of the valve and on other parameters such as the size of the valve opening and the gas pressure. The apparatus is therefore calibrated before use such that the gas volume per pulse may be accurately deduced and regulated.

The pulsed gas flow passes through a humidifier in the form of a nebulizer 8, which will be described in more detail below, and thereafter is supplied directly to the lungs of a patient via a narrow orifice jet 9 secured to the end of a length of low compliance flexible tubing 10. The jet 9 directs gas into a suitable cannula (not shown) leading to the lungs of the patient. When the valve 5 is open, the pressure in the tube 10 upstream of the jet 9 may be in the order of 100–200 kPa, but reduces greatly upon expansion into the low compliance lungs of the patient to approximately 1–4 kPa.

The nebulizer 8 is illustrated in FIG. 2, and comprises a chamber 11 having a gas inlet 12 in the form of a cannula, and an outlet 13. The cannula terminates in a tube 14 of relatively small cross-section which maintains a rapid gas flow rate into the chamber. Disposed beneath the chamber 11 is a small reservoir 15 having a liquid inlet 16 and communicating with the chamber via a conduit 17 which terminates above water level in the reservoir, and via a narrow tube 18 which extends almost to the bottom wall of the reservoir. The tube 18 passes through one side of the gas inlet cannula, and is bent through 90° so as to extend within the tube 14 coaxially therewith. A spherical stainless steel anvil 19 is located within the chamber 11 on the axis of the tubes 14, 18 and spaced from the ends thereof.

The diameter of tube 14 may be 2–3 mm and tube 18 may have an OD of 1 mm and 1D of ½ mm, projecting 2–3 mm from the end of tube 14. The anvil may be of 6–10 mm diameter and positioned 5–10 mm from the end of tube 18.

In operation, when the valve 5 is open, the gas pressure within the chamber 11 rises sharply and since the reservoir communicates with the chamber via conduit 17 this causes liquid to be forced up the tube 18. Tube 18 is designed to act as a fluid resistance and limit the maximum rate of water delivery in relation to the available gas pressure. The liquid emerges from the tip of the tube 18 and is entrained and nebulized by the rapidly moving gas flow. The water droplets impinge on the anvil 19 which causes a further reduction in droplet size before being carried out of the chamber via the outlet 13. Larger drops which may form within the chamber fall to its base and return to the reservoir via the conduit 17. The nebulizer preferably includes an electric heating element (not shown) such that the droplet size is minimised and the gas supplied to the patient is suitably warmed.

The reservoir 15 has a relatively small volume as compared with conventional nebulizers of this type, and therefore is of low compliance which is important where substantial square wave gas pulses are desired. Thus, frequent refilling is required and this is achieved by means of a pump 20 which is connected via a line 21 to a suitable liquid source such as a constant gravity infusion pack of sterile water (not shown). A one way valve 22 is provided between the pump 20 and the reservoir 15 to prevent reverse liquid flow upon pressure increases within the nebulizing chamber.

In accordance with the invention, the reservoir 15 is refilled with a known volume of liquid at intermittent intervals, and during refilling the valve 5 is maintained in its closed condition such that the gas pressure in the chamber 11 is minimised. Thus, the pump 20 is connected to the control circuitry 6 such that during operation of the pump the valve 5 is held shut. Since the pressure in the chamber is substantially constant during refilling of the reservoir, undesirable liquid boluses are not formed and moreover filling can be at a controlled rate. In the preferred embodiment, the pump 20 is adapted to deliver liquid to the reservoir at a precise flow rate of 1 ml/sec, and the control circuitry is adapted to operate the pump for periods ranging between $\frac{1}{2}$ and 5 seconds such that the volume of liquid passed into the reservoir during each refilling cycle may be selected from a range of $\frac{1}{2}$ to 5 ml.

It will be seen that the overall quantity of liquid delivered to the patient depends on the time period between the refilling cycles and on the volume delivered during each cycle and may thus be precisely regulated. In one embodiment the control circuitry 6 is adapted to actuate the pump at regular intervals, for example every 1 to 2 minutes. Alternatively, the physician may apply clinical judgement in this regard and may actuate the pump at intermittent intervals himself. To avoid an excess volume of liquid being supplied to the lungs, there will generally be a period of time between the reservoir emptying and the next refilling cycle being actuated, and the reservoir may on average be empty for something in the order of one third of the overall cycle time. Experience shows that this is not harmful to the patient.

I claim:

1. Gas humidifying apparatus comprising a chamber arranged to receive a fluctuating gas flow from an oscillating valve means, a liquid reservoir communicating with the chamber such that in use liquid from the reservoir passes into the chamber and is entrained in droplet form by the flow of gas, liquid supply means intermittently operable to introduce a predetermined quantity of liquid into the reservoir, and control means adapted to maintain said valve means in a closed condition during operation of said liquid supply means.

2. Apparatus as claimed in claim 1 wherein said liquid supply means comprises a pump which communicates with the reservoir via a non-return valve.

3. Apparatus as claimed in claim 1 comprising heating means arranged to maintain the apparatus at a desired temperature.

4. Apparatus as claimed in claim 1 wherein the arrangement of the reservoir and the chamber is such that liquid is forced into the chamber in response to increases in gas pressure therein, the liquid being introduced into the chamber via a small diameter tube which is arranged such that the liquid emerging therefrom is entrained and nebulized by the gas flowing into the chamber, an anvil being located within the chamber upon which the entrained liquid impinges such that the size of the droplets is reduced before the humidified gas emerges from the chamber via an outlet opening thereof.

5. Apparatus as claimed in claim 1 wherein the overall volume of the nebulizing chamber and the reservoir is less than 10 ml.

6. Apparatus as claimed in claim 1 wherein said control means adapted to maintain the valve means in a closed condition during refilling of the reservoir forms part of control circuitry of the apparatus which is additionally adapted to control the frequency of the oscillating valve and the operating cycle of the liquid supply means.

7. A high frequency positive pressure ventilation system incorporating gas humidifying apparatus as claimed in claim 1.

8. A system as claimed in claim 7 adapted to deliver drugs to a patient, wherein metered quantities of the drug or drugs are added to the liquid either before or after the introduction thereof into the reservoir.

9. A method of humidifying a fluctuating gas flow from an oscillating valve means wherein liquid from a reservoir is entrained in droplet form by the flow of gas in a chamber communicating with said reservoir, comprising intermittently introducing a predetermined quantity of liquid into the reservoir while maintaining said valve means in a closed condition.

* * * * *